United States Patent
Mazzotta et al.

(10) Patent No.: US 10,052,276 B2
(45) Date of Patent: Aug. 21, 2018

(54) FRAGRANCE TREATMENT COMPLEX

(71) Applicant: Beauty Boost, Inc., Larchmont, NY (US)

(72) Inventors: Paul F. Mazzotta, Reading, PA (US); Josephine Sullivan, Larchmont, NY (US)

(73) Assignee: HBWC Corporation, Quiogue, NY (US)

( * ) Notice: Subject to any disclaimer, the term of this patent is extended or adjusted under 35 U.S.C. 154(b) by 36 days.

(21) Appl. No.: 15/429,539

(22) Filed: Feb. 10, 2017

(65) Prior Publication Data

US 2017/0231892 A1   Aug. 17, 2017

Related U.S. Application Data

(60) Provisional application No. 62/294,636, filed on Feb. 12, 2016.

(51) Int. Cl.
| | |
|---|---|
| *A61K 8/02* | (2006.01) |
| *A61K 8/81* | (2006.01) |
| *A61K 8/73* | (2006.01) |
| *A61K 8/49* | (2006.01) |
| *A61K 8/34* | (2006.01) |
| *A61K 8/92* | (2006.01) |
| *A61K 8/67* | (2006.01) |
| *A61K 8/31* | (2006.01) |
| *A61Q 13/00* | (2006.01) |

(52) U.S. Cl.
CPC .............. *A61K 8/8152* (2013.01); *A61K 8/31* (2013.01); *A61K 8/34* (2013.01); *A61K 8/4993* (2013.01); *A61K 8/678* (2013.01); *A61K 8/737* (2013.01); *A61K 8/922* (2013.01); *A61Q 13/00* (2013.01)

(58) Field of Classification Search
CPC .................................................. A61K 8/8152
See application file for complete search history.

(56) References Cited

U.S. PATENT DOCUMENTS 7,255,718 B1 * 8/2007 Akram ................ A61K 8/4946
                                                              8/405
9,265,711 B2   2/2016 Kulkarni et al.

* cited by examiner

*Primary Examiner* — Arrie L Reuther
(74) *Attorney, Agent, or Firm* — Miller Law Group, PLLC

(57) ABSTRACT

A fragrance extending product containing a fragrance treatment complex is disclosed to extend the effective life of the fragrance carried by a fragrance-bearing product, such as perfume and cologne. The fragrance extending product is preferably a spray-on product that can be applied over the top of the fragrance-bearing product. The fragrance treatment complex resists the evaporation of the perfume oils from the fragrance-bearing product, as well as resists removal caused by abrasion and binding with water. The fragrance treatment complex formulation includes acrylates/octylacrylamide copolymer; Polyquaternium 11, a quaternized copolymer; guar hydroxypropyltrimonium chloride, a cationic polymer, and cocamidopropyl PG-dimonium chloride, a phospholipid. Tests have shown that the effective life of a fragrance-bearing product can be more than twelve hours with the application of the fragrance treatment complex over the fragrance-bearing product previously applied to a human body. A long lasting fragrance bearing product is also disclosed using the fragrance treatment complex.

19 Claims, 1 Drawing Sheet

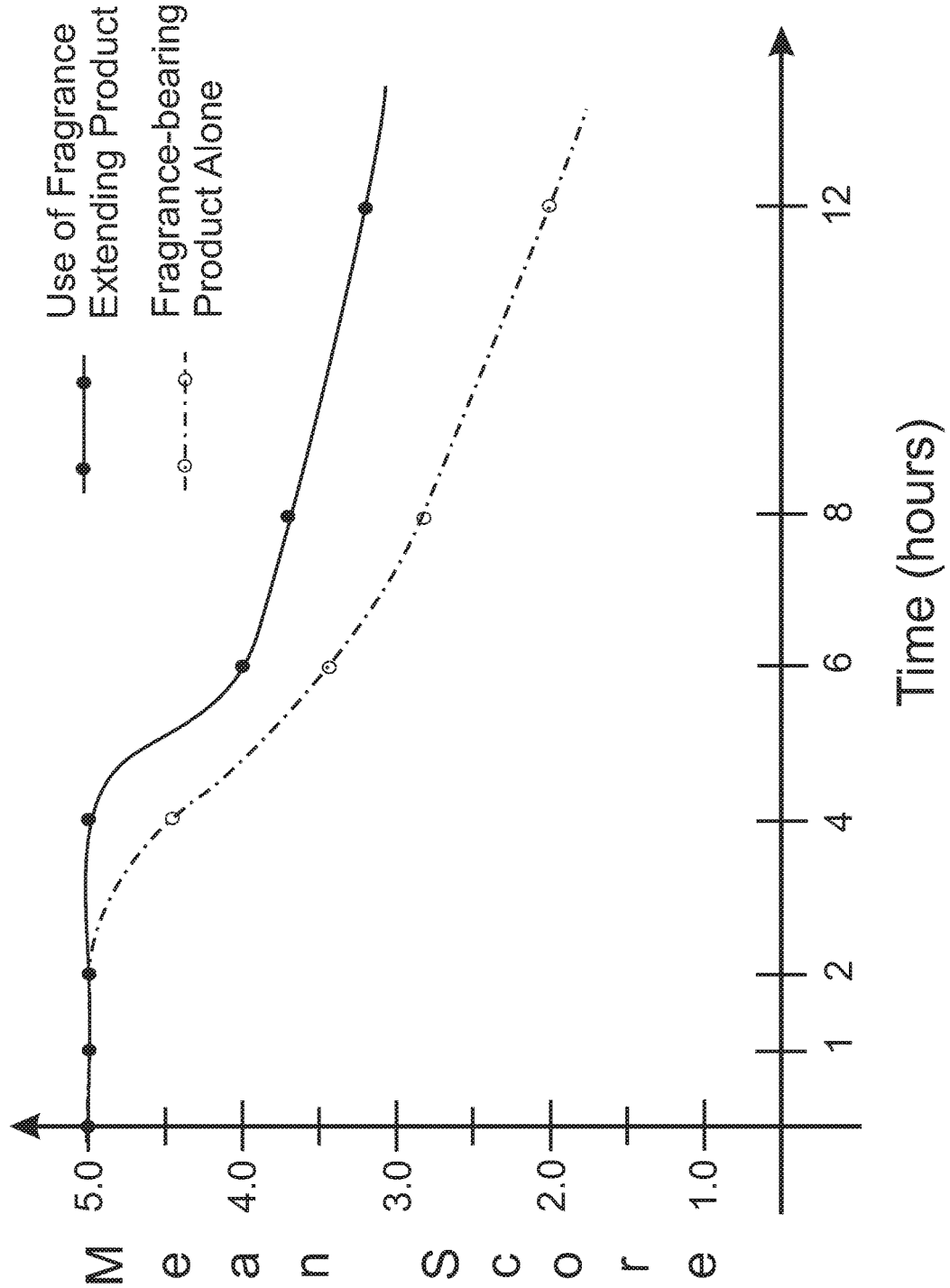

FRAGRANCE TREATMENT COMPLEX

CROSS-REFERENCE TO RELATED APPLICATIONS

This application claims domestic priority on U.S. Provisional Patent Application Ser. No. 62/294,636, filed on Feb. 12, 2016, the content of which is incorporated herein.

FIELD OF THE INVENTION

The present invention relates generally to perfumes, colognes and other products carrying a fragrance when applied to the human body, and more particularly, to a fragrance treatment complex that can be added to the fragrance-bearing product to extend the effective life of the fragrance.

BACKGROUND OF THE INVENTION

Fragrance-bearing products, such as perfume and cologne, carry specific fragrances that are desired by the person applying the product to his or her body. Over a period of time, the fragrance dissipates and can no longer be detected. Typically, fragrance-bearing products, such as perfume, are formulated with various ingredients, ranging from alcohol, solvent, and perfume oils that are obtained from natural sources and also from synthetic creations. These products evaporate over time taking the fragrance with them. Accordingly, a problem with conventional fragrance-bearing products is that these products do not contain ingredients or components that are designed to increase the effective life of the fragrance and allow the fragrance to last for a longer period of time.

Conventional fragrance-bearing products do not resist evaporation from the human body. Furthermore, conventional fragrance-bearing products do not have properties that resist abrasion or removal from the skin by rubbing. Conventional fragrance-bearing products have no resistance to binding with water and becoming diluted, and thus reducing the effective life of the fragrance. Also, conventional fragrance-bearing products have no ability to provide a sustained release of the fragrance from the product applied to the skin. Presently, no treatment for fragrance-bearing products is available to facilitate the extension of the effective life of a fragrance-bearing product.

In U.S. Pat. No. 9,265,711, granted to Rupali A. Kulkarni, et al., on Feb. 23, 2016, a cosmetic composition that enables the perfume component of a fragrance-bearing product to be resistant to water and sweat, and thus be fixed for an extended period of time in a watertight manner on the skin. This composition includes a fragrance mixed with a fragrance fixing complex consisting of a hydrophobic alcohol soluble, carboxylated acrylates/octylacrylamide copolymer and a hydrolyzed jojoba ester in which the total amount of fragrance can be reduced though giving the same feeling to the consumer. The Kulkarni composition includes the fragrance and a copolymer intended to resist water and does not disclose a fragrance extending product that can be placed over a previous application of a fragrance bearing product to the user's skin. Furthermore, the Kulkarni composition does not contain components that allow the composition to attract to the skin of the person wearing the composition.

Presently, the only method known to extend the effective life of a fragrance applied to the human body is to increase the percentage of the perfume oils in the formulation of the fragrance-bearing product. While this process will extend the effective life of the fragrance by providing more oils to be evaporated from the skin, the increase of perfume oils significantly increases the cost of formulating the fragrance-bearing product, and therefore, increases the cost borne by the consumer.

It would be desirable to provide a treatment product that would be operative to increase the effective life of a fragrance-bearing product once placed onto the human body.

SUMMARY OF THE INVENTION

It is an object of this invention to overcome the disadvantages of the prior art by providing a fragrance treatment complex that will extend the effective life of a fragrance-bearing product.

It is another object of this invention to provide a fragrance extending product containing a fragrance treatment complex that can be applied to the human body after the application of the fragrance-bearing product to extend the life of the fragrance.

It is a feature of this invention that the fragrance extending product can be sprayed onto the human body to cover over the fragrance-bearing product previously applied to the body.

It is an advantage of this invention that the fragrance extending product is fragrance free.

It is another advantage of this invention that the fragrance treatment complex slows the evaporation rate of the fragrance-bearing product.

It is still another advantage of this invention that the fragrance treatment complex allows the fragrance-bearing product to have a sustained release of the perfume oils establishing the fragrance of the product.

It is yet another advantage of this invention that the fragrance treatment complex provides a resistance for the fragrance-bearing product to be removed from the human body by binding with water or through abrasion or rubbing of the fragrance-bearing product.

It is another feature of this invention that the fragrance treatment complex is formulated to allow fragrance-bearing products to last longer by providing a unique formula disposed within a cosmetically acceptable carrier solution to create a fragrance extending product.

It is still another feature of this invention that the formula of the fragrance treatment complex includes a copolymer, specifically, acrylates/octylacrylamide copolymer; a quaternized copolymer, specifically, Polyquaternium 11; a catatonic polymer, specifically, guar hydroxypropyltrimonium chloride, and a phospholipid, specifically, cocamidopropyl PG-dimonium chloride.

It is yet another feature of this invention that tests have shown that the application of the fragrance treatment complex to a fragrance-bearing product can achieve an effective life of the fragrance at more than twelve hours after application of the fragrance-bearing product to the human body.

It is another advantage of this invention that the fragrance extending product does not carry a fragrance that either adds to or conflicts with the fragrance carried by the fragrance-bearing product.

It is still another object of this invention to provide a fragrance extending product containing a fragrance treatment complex that can be conveniently applied over top of the fragrance-bearing product after being applied to the human body.

It is a further object of this invention to provide a fragrance extending product containing a fragrance treatment complex that is inexpensive to manufacture, easy to utilize, and simple and effective in use.

These and other objects, features and advantages are accomplished according to the instant invention by providing a fragrance extending product containing a fragrance treatment complex that can be applied to a fragrance-bearing product to extend the effective life of the fragrance carried thereby. The fragrance extending product is preferably a spray-on product that can be applied over the top of the fragrance-bearing product. The fragrance treatment complex resists the evaporation of the perfume oils from the fragrance-bearing product, as well as resists removal caused by abrasion and binding with water. The fragrance treatment complex formulation includes acrylates/octylacrylamide copolymer; Polyquaternium 11, a quaternized copolymer; guar hydroxypropyltrimonium chloride, a cationic polymer, and cocamidopropyl PG-dimonium chloride, a phospholipid. Tests have shown that the effective life of a fragrance-bearing product can be more than twelve hours with the application of the fragrance treatment complex over the fragrance-bearing product previously applied to a human body. A long lasting fragrance-bearing product can also utilize the fragrance treatment complex.

BRIEF DESCRIPTION OF THE DRAWINGS

The foregoing and other objects, features, and advantages of the invention will appear more fully hereinafter from a consideration of the detailed description that follows, in conjunction with the accompanying sheet of drawings. This drawing is for illustrative purposes and is not to be construed as defining the limits of the invention.

The drawing figure is a graphic representation of the test results showing the efficacy of the fragrance extending product in sustaining fragrance of a fragrance-bearing product.

DETAILED DESCRIPTION OF THE PREFERRED EMBODIMENT

A fragrance treatment complex incorporating the principles of the instant invention is disclosed herein. The fragrance treatment complex is designed to be applied to a fragrance-bearing product, such as perfume and cologne, to extend the effective life of the fragrance carried by the fragrance-bearing product for twelve hours or more. In a preferred embodiment, the fragrance treatment complex is applied as a spray-on product that is applied over the top of a fragrance-bearing product that has been previously applied to the skin of the person wearing the fragrance-bearing product who desires to extend the life of the fragrance.

The preferred embodiment of the instant invention presents a long lasting fragrance treatment complex specifically formulated to help fragrance-bearing products, such as perfume, last longer and is a formulation disposed within a cosmetically acceptable carrier solution. The formulation for the fragrance treatment complex contains acrylates/octylacrylamide copolymer; Polyquaternium 11, a quaternized copolymer; guar hydroxypropyltrimonium chloride, a cationic polymer; and cocamidopropyl PG-dimonium chloride, a phospholipid, and would account for 2.5-5.0% by weight of the finished product incorporating the fragrance treatment complex.

Acrylates/octylacrylamide copolymer is a hydrophobic, high molecular weight carboxylated acrylic copolymer. Acrylates/octylacrylamide copolymer film formation properties help maintain active ingredients such as perfume/ aroma oils on the site of application of the fragrance-bearing product by resisting evaporation thereof, as well as resisting abrasion or rub-off. Acrylates/octylacrylamide copolymer also provides a resistance to the binding of the underlying fragrance-bearing product to water, thus establishing a sustained release of the fragrance from the fragrance-bearing product. Because acrylates/octylacrylamide copolymer is inherently moisture resistant, this polymer also gives the fragrance-bearing product water resistant properties.

Polyquaternium 11 is a quaternized copolymer conventionally used for skin care. This quaternized copolymer is an aqueous solution of cationic polymers of different charge density and different degrees of conditioning. Polyquaternium 11 has a weight composition of 67% VP, a solids content of 19-21, and a charge density of 0.8 meq/g at pH 7.

Guar hydroxypropyltrimonium chloride is a cationic polymer that provides dual benefits of conditioning and viscosity. The cationic charge of this polymer makes the fragrance treatment complex attractive to anionic surfaces such as skin. This component creates a film on the skin over the fragrance-bearing product to help keep the fragrance carried thereby from rubbing off through abrasion.

Cocamidopropyl PG-dimonium chloride, chemically described as cocamidopropyl phosphatidyl PG-dimonium chloride, is a coconut oil derived phospholipid composed predominantly of diester and triester phosphatides with multiple chain groups. In addition to topically simulating the properties displayed by the polar stratum corneum lipids, cocamidopropyl PG-dimonium chloride displays a broad range of functional attributes including anti-irritation effects when combined with alcohol, unusually high substantivity, long-lasting skin conditioning, and a broad spectrum antimicrobial activity.

The carrier for the fragrance treatment complex is denatured alcohol mixed with Bergamotta Oil, Vitamin E, Isododecane, and a Lipophilic Complex to provide a cosmetically acceptable carrier that will benefit the skin of the recipient of the fragrance treatment complex. The Lipophilic Complex is a mixture of one or more of *Glycine Soja* (Soy) Oil, *Vitis Vinifera* (Grapeseed) Oil, *Prunus Armeniaca* (Apricot) Kernel Oil, *Carthamus Tinctorius* (Safflower) Seed Oil, *Borago Officinalis* (Borage) Seed Oil, *Oenothera Biennis* (Evening Primrose) Oil, *Linum Usitatissimum* (Flax Linseed) Oil and Tocopherol (Vitamin E), all of which is in the range of 0.01-0.1% by weight of the final fragrance extending product to be defined in greater detail below. The Lipophilic Complex contains skin care oils that offset the effects of the alcohol in the carrier with respect to the skin. The same effect is provided by the utilization of Bergamotta Oil, Isododecane and Vitamin E in the carrier.

The fragrance treatment complex becomes an essential ingredient in combination with the above-defined carrier to create a fragrance extending product that is to be applied over a fragrance bearing product to extend the life of the fragrance carried thereby. A polymer solution is created by combining three of the four above-described components in the following ratios: 97-99% by weight of cocamidopropyl PG-dimonium chloride, 0.5-2.0% by weight of Polyquaternium 11, and 0.1-0.5% by weight of guar hydroxypropyltrimonium chloride. Because of the respective volumes of the components creating the fragrance extending product as defined in greater detail below, the acrylates/octylacrylamide copolymer is added individually with the above-defined polymer solution when the fragrance extending product is formed.

In the preferred embodiment of the polymer solution, 896.31 grams (98.8% by weight) of the cocamidopropyl PG-dimonium chloride is mixed with 9.07 grams (1.0% by weight) of Polyquaternium 11 added slowly and allowed to melt fully until 1.81 grams (0.2% by weight) of guar hydroxypropyltrimonium chloride is added slowly with a sifter until all ingredients are thoroughly mixed and thoroughly blended to create a batch of 2.0 pounds (907.2 grams) of the polymer solution which is utilized as a component in the manufacture of the fragrance extending product to be described in greater detail below.

The fragrance extending product is created by combining the fragrance treatment complex with the carrier described above with the components thereof being mixed in the following ratios: 90-97% by weight of denatured alcohol, 2-5% by weight of acrylates/octylacrylamide copolymer (the individually added component of the fragrance treatment complex), 0.5-1.0% by weight of Bergamotta Oil, 0.01-1.0% by weight of Vitamin E, 0.01-1.0% by weight of Isododecane, 0.01-1.0% by weight of the Lipophilic Complex described above, and 0.01-1.0% of the polymer solution described above and containing the remaining three components of the fragrance treatment complex.

In the preferred embodiment of the fragrance extending product, 393581.92 grams (95.35% by weight) of denatured alcohol is added to an appropriately sized vessel with a lightening mixer. 14447.16 grams (3.50% by weight) of Dermacryl 79, an acrylates/octylacrylamide copolymer produced by Akso Knobel, is added slowly to the denatured alcohol with a sifter and allowed to melt thoroughly before adding 3095.82 grams (0.75% by weight) of Bergamotta Oil followed by the addition in order of 412.78 grams (0.1% by weight) of each of Isododecane, the lipophilic complex, Vitamin E, and the polymer complex to produce 909.09 pounds of the fragrance extending product to be bottled and distributed. It should be noted that the acrylates/octylacrylamide copolymer component added to the fragrance extending product is Dermacryl 79, produced by Akso Knobel, rather than Dermacryl AQF which has only water resistance properties.

Accordingly, the ranges of the components of the fragrance treatment complex would be 95-99% by weight of acrylates/octylacrylamide copolymer, 0.01 to 0.05% by weight of Polyquaternium 11, 0.001-0.01% by weight of guar hydroxypropyltrimonium chloride, and 1-5% by weight of cocamidopropyl PG-dimonium chloride. Using the preferred component volumes described above to create the fragrance extending product, the respective components of the fragrance treatment complex would have the following preferred ratios: 97.22% by weight of acrylates/octylacrylamide copolymer, 0.028% by weight of Polyquaternium 11, 0.006% by weight of guar hydroxypropyltrimonium chloride, and 2.74% by weight of cocamidopropyl PG-dimonium chloride.

In application, the fragrance extending product is sprayed over top of the fragrance-bearing product previously applied to an area of the skin by the user. The denatured alcohol will freely evaporate leaving the Bergamotta oil, the lipophilic complex and Vitamin E to nourish the skin to which the fragrance extending product is applied, while the fragrance treatment complex sustains the release of the perfume oils from the fragrance-bearing product by copolymer film over the fragrance-bearing product to resist binding with water and to resist removal by abrasion and rubbing.

Tests conducted by the Essex Testing Clinic, Inc. have shown that the fragrance extending product contained a cosmetically acceptable carrier and that the fragrance treatment complex was effective in extending the effective life of the fragrance carried by the fragrance-bearing product. More specifically, 58 subjects, including 11 males and 47 females ranging in age between 29 and 77 years, were tested by applying the fragrance extending product formed as described above to the subject's back. Approximately 0.2 ml of the fragrance extending product was placed on a square of cotton fabric attached to semi-occlusive surgical tape which was then applied to the back of each subject for 24 hours, and repeated every 48 to 72 hours until 9 applications had been applied to establish an induction phase. Two weeks after the induction phase, the same subjects were again subjected to the same test for 24 hours as a challenge phase. Two of the subjects terminated the test for reasons unrelated to the test, leaving 56 subjects. None of the subjects reported any skin reactions, thus leading to the conclusion that the fragrance extending product was not associated with any skin irritation or allergic contact dermatitis in human subjects.

Additional testing of the Essex Testing Clinic, Inc. was conducted to determine if the fragrance treatment complex, as applied through the use of the fragrance extending product, would effectively extend the effective life of the fragrance-bearing product. Thirty women subjects were selected with ages ranging from 18 to 70 years to test the efficacy of the fragrance treatment complex. Each subject was asked to bring their own fragrance-bearing product to the test. Each subject had their own fragrance-bearing product applied to both the right and left wrists, and then the fragrance extending product was applied to one of the wrists in a random manner vis-a-vis all of the subjects. At repeated intervals, a trained technician evaluated the strength of the fragrance on each of the subject's two wrists grading the strength on the following scale: 5 for a strong scent, 4 for a mild scent, 3 for a moderate scent, 2 for a light scent and 1 for no scent detected. The evaluation intervals were set at one hour, two hours, four hours, six hours, 8 hours and 12 hours after application of the fragrance-bearing product. A last evaluation by the subject was provided at 24 hours after application of the fragrance bearing product.

The following table, which is graphically depicted in the drawing figure, presents a summary of the mean appearance scores of the thirty subjects with respect to the use of the fragrance extending product as compared to the use of the fragrance-bearing product alone:

|  | Use of Fragrance Extending Product | | Fragrance-Bearing Product Alone | | |
| --- | --- | --- | --- | --- | --- |
|  | Mean Score | % Change from Baseline | Mean Score | % Change from Baseline | % Difference |
| Baseline | 5.0 |  | 5.0 |  |  |
| 1 Hour | 5.0 | 0% | 5.0 | 0% | 0% |
| 2 Hours | 5.0 | 0% | 5.0 | 0% | 0% |
| 4 Hours | 5.0 | 0% | 4.4 | 12% | 14% |
| 6 Hours | 4.0 | 20% | 3.4 | 32% | 18% |
| 8 Hours | 3.7 | 26% | 2.8 | 44% | 24% |
| 12 Hours | 3.2 | 36% | 2.0 | 60% | 60% |

The conclusion of the independent test was that the comparison of the fragrance extender product as compared to the use of the fragrance-bearing product alone resulted in the use of the fragrance extending product over top of the fragrance-bearing product extended the scent of the fragrance-bearing product longer than when the fragrance-bearing product was worn without the fragrance extending product. As noted above, the mean result at 12 hours showed a 60% increase in the strength of the scent of the fragrance by using the fragrance extending product.

In addition, each of the subjects was required to answer a questionnaire after 24 hours of wearing the fragrance extending product. 84% of the subjects agreed that their respective fragrance of their fragrance-bearing product with the fragrance extending product applied lasted twice as long as they would have normally experienced with only their fragrance-bearing product used alone. These subjects agreed that the use of this fragrance extending product would result in their enjoyment of their respective fragrance more. A total of 69% of the subjects could still smell their respective fragrance the morning after their testing on the test site (approximately 24 hours later) on which the fragrance extending product had been applied. Many of them reported still being able to smell their fragrance scent 36 hours after application.

This fragrance treatment complex can also be utilized to provide a long lasting fragrance-bearing product by incorporating the fragrance treatment complex into the formulation of the fragrance-bearing product with some changes to accommodate the properties of the fragrance oils, i.e. perfume or aroma oils. Because of the properties of the perfume or aroma oils, these oils do not want to bond with the skin. Accordingly, the cationic properties of the fragrance treatment complex have to be increased to make the fragrance-bearing product attract to the skin and allow the scent to be sustained in a manner similar to the application of the fragrance extending product, as described above.

As with the fragrance extending product described above, the fragrance treatment complex is utilized as a polymer solution that contains three of the four components of the fragrance treatment complex, with the fourth component (acrylates/octylacrylamide copolymer) being accounted for individually because of the respective volumes. However, an additional volume of the Polyquaternium 11 is required to provide satisfactory cationic properties to combine with the aroma oils in the fragrance-bearing product to make the fragrance-bearing product attract to anionic human skin. As noted above, the skin care oils in the Lipophilic Complex and other components offset the drying effects of alcohol in the carrier and nourish the skin.

Fragrance-bearing products are typically defined in one of five categories, including Eau de Toilette, Eau de Cologne, Eau de Perfume, Perfume and an Aromatic Splash. The differences between these categories of fragrance-bearing products primarily being the type and volume of perfume or aroma oils in the respective formula. Accordingly, the individual formulas will vary accordingly, but generally a long lasting fragrance-bearing product containing the principles of the instant invention can be obtained by combining the following components mixed in the following ratios: 65-85% by weight of denatured alcohol, 1-5% by weight of acrylates/octylacrylamide copolymer (the individually added component of the fragrance treatment complex), 0.5-1.0% by weight of Bergamotta Oil, 1-15% perfume blend (fragrance oils), 10-25% deionized water, 0.5-2.0% of Polyquaternium 11, 0.01-1.0% by weight of Vitamin E, 0.01-1.0% by weight of Isododecane, 0.01-1.0% by weight of the Lipophilic Complex described above, and 0.01-1.0% of the polymer solution described above and containing the remaining three components of the fragrance treatment complex.

In the preferred embodiment of an Eau de Toilette, 2495.37 grams (73.35% by weight) of denatured alcohol is added to an appropriately sized vessel with a lightening mixer operated at slow speed to create a vortex. Then, 119.07 grams (3.50% by weight) of Dermacryl 79, an acrylates/octylacrylamide copolymer produced by Akso Knobel, is added slowly to the denatured alcohol with a sifter and allowed to melt thoroughly before adding 25.52 grams (0.75% by weight) of Bergamotta Oil followed by 136.08 grams (4.0% by weight) of Perfume Blend (Fracas) and 578.34 grams (17.0% by weight) of deionized water to the mixture. Finally, adding 34.02 grams (1.0% by weight) of Polyquaternium 11, and 3.40 grams (0.1% by weight) of each of Isododecane, the Lipophilic Complex, Vitamin E, and the Polymer Complex will produce 120 ounces of the Eau de Toilette (fragrance-bearing product) to be bottled and distributed.

In the preferred embodiment of an Eau de Cologne, 2359.29 grams (69.35% by weight) of denatured alcohol is added to an appropriately sized vessel with a lightening mixer operated at slow speed to create a vortex. Then, 119.07 grams (3.50% by weight) of Dermacryl 79, an acrylates/octylacrylamide copolymer produced by Akso Knobel, is added slowly to the denatured alcohol with a sifter and allowed to melt thoroughly before adding 25.52 grams (0.75% by weight) of Bergamotta Oil followed by 102.06 grams (3.0% by weight) of Perfume Blend (Fracas) and 748.44 grams (22.0% by weight) of deionized water to the mixture. Finally, adding 34.02 grams (1.0% by weight) of Polyquaternium 11, and 3.40 grams (0.1% by weight) of each of Isododecane, the Lipophilic Complex, Vitamin E, and the Polymer Complex will produce 120 ounces of the Eau de Cologne (fragrance-bearing product) to be bottled and distributed.

In the preferred embodiment of an Eau de Perfume, 2359.29 grams (69.35% by weight) of denatured alcohol is added to an appropriately sized vessel with a lightening mixer operated at slow speed to create a vortex. Then, 119.07 grams (3.50% by weight) of Dermacryl 79, an acrylates/octylacrylamide copolymer produced by Akso Knobel, is added slowly to the denatured alcohol with a sifter and allowed to melt thoroughly before adding 25.52 grams (0.75% by weight) of Bergamotta Oil followed by 272.16 grams (8.0% by weight) of Perfume Blend (Fracas) and 578.34 grams (17.0% by weight) of deionized water to the mixture. Finally, adding 34.02 grams (1.0% by weight) of Polyquaternium 11, and 3.40 grams (0.1% by weight) of each of Isododecane, the Lipophilic Complex, Vitamin E, and the Polymer Complex will produce 120 ounces of the Eau de Perfume (fragrance-bearing product) to be bottled and distributed.

In the preferred embodiment of a Perfume, 2359.29 grams (69.35% by weight) of denatured alcohol is added to an appropriately sized vessel with a lightening mixer operated at slow speed to create a vortex. Then, 119.07 grams (3.50% by weight) of Dermacryl 79, an acrylates/octylacrylamide copolymer produced by Akso Knobel, is added slowly to the denatured alcohol with a sifter and allowed to melt thoroughly before adding 25.52 grams (0.75% by weight) of Bergamotta Oil followed by 510.30 grams (15.0% by weight) of Perfume Blend (Fracas) and 340.20 grams (10.0% by weight) of deionized water to the mixture. Finally, 34.02 grams (1.0% by weight) of Polyquaternium 11, and 3.40 grams (0.1% by weight) of each of Isododecane, the Lipophilic Complex, Vitamin E, and the Polymer Complex will produce 120 ounces of Perfume (fragrance-bearing product) to be bottled and distributed.

In the preferred embodiment of an Aromatic Splash, 2325.27 grams (68.35% by weight) of denatured alcohol is added to an appropriately sized vessel with a lightening mixer operated at slow speed to create a vortex. Then, 119.07 grams (3.50% by weight) of Dermacryl 79, an acrylates/octylacrylamide copolymer produced by Akso Knobel, is added slowly to the denatured alcohol with a sifter and allowed to melt thoroughly before adding 25.52 grams (0.75% by weight) of Bergamotta Oil followed by 51.03 grams (1.5% by weight) of Perfume Blend (Fracas) and 833.49 grams (24.5% by weight) of deionized water to the mixture. Finally, adding 34.02 grams (1.0% by weight) of Polyquaternium 11, and 3.40 grams (0.1% by weight) of each of Isododecane, the Lipophilic Complex, Vitamin E, and the Polymer Complex will produce 120 ounces of Aromatic Splash (fragrance-bearing product) to be bottled and distributed.

It will be understood that changes in the details, materials, steps and arrangements of parts which have been described and illustrated to explain the nature of the invention will occur to and may be made by those skilled in the art upon a reading of this disclosure within the principles and scope of the invention. The foregoing description illustrates the preferred embodiments of the invention; however, concepts, as based upon the description, may be employed in other embodiments without departing from the scope of the invention. The invention is not otherwise limited, except for the recitation of the claims set forth below.

Having thus described the invention, what is claimed is:

1. A fragrance treatment complex, comprising:
   95-99% by weight of acrylates/octylacrylamide copolymer;
   1-5% by weight of cocamidopropyl PG-dimonium chloride;
   0.01-0.05% by weight of Polyquaternium 11; and
   0.001-0.01% by weight of guar hydroxypropyltrimonium chloride.

2. The fragrance treatment complex of claim 1 wherein said fragrance treatment complex is added to a cosmetically acceptable carrier to create a fragrance extending product to be applied to a fragrance-bearing product previously placed on the skin of a human.

3. The fragrance treatment complex of claim 2 wherein said carrier comprises:
   denatured alcohol;
   Bergamotta Oil;
   Vitamin E;
   Isododecane; and
   a Lipophilic Complex.

4. The fragrance treatment complex of claim 3 wherein said Lipophilic Complex comprises one or more of:
   *Glycine Soja* (Soy) Oil;
   *Vitis Vinifera* (Grapeseed) Oil;
   *Prunus Armeniaca* (Apricot) Kernel Oil;
   *Carthamus Tinctorius* (Safflower) Seed Oil;
   *Borago Officinalis* (Borage) Seed Oil;
   *Oenothera Biennis* (Evening Primrose) Oil; and
   *Linum Usitatissimum* (Flax Linseed) Oil.

5. The fragrance treatment complex of claim 4 wherein said Lipophilic Complex further comprises Tocopherol (Vitamin E).

6. The fragrance treatment complex of claim 5 wherein said fragrance treatment complex comprises:
   97.22% by weight of acrylates/octylacrylamide copolymer;
   0.03% by weight of Polyquaternium 11;
   0.006% by weight of guar hydroxypropyltrimonium chloride; and
   2.74% by weight of cocamidopropyl PG-dimonium chloride.

7. The fragrance treatment complex of claim 6 wherein said fragrance extending product comprises:
   95.35% by weight of denatured alcohol;
   3.50% by weight of acrylates/octylacrylamide copolymer;
   0.75% by weight of Bergamotta Oil;
   0.1% by weight of Isododecane;
   0.1% by weight of said lipophilic complex;
   0.1% by weight of Vitamin E; and
   0.1% by weight of a polymer solution.

8. The fragrance treatment complex of claim 7 wherein said polymer solution comprises three of the four components of the components of the fragrance treatment complex, including said Polyquaternium 11, said guar hydroxypropyltrimonium chloride, and said cocamidopropyl PG-dimonium chloride.

9. The fragrance treatment complex of claim 8 wherein said fragrance extending product is created by placing the denatured alcohol into an appropriately sized vessel with a lightening mixer set on slow speed until a vortex is generated; then adding the acrylates/octylacrylamide copolymer slowly to the denatured alcohol with a sifter and allowed to melt thoroughly; then adding the Bergamotta Oil followed by the addition of Isododecane, the lipophilic complex, Vitamin E, and the polymer solution.

10. The fragrance treatment complex of claim 9 wherein said polymer solution is created by placing the placing the cocamidopropyl PG-dimonium chloride into an appropriately sized vessel with a lightening mixer set on slow speed until a vortex is generated, then adding the Polyquaternium 11 slowly and allowed to thoroughly melt before adding the guar hydroxypropyltrimonium chloride slowly with a sifter and mixing thoroughly.

11. A fragrance extending product for application over a fragrance-bearing product applied to human skin to sustain the release of fragrance from the fragrance-bearing product, comprising:
    2.5-5.0% by weight of a fragrance treatment complex including:
       95-99% by weight of acrylates/octylacrylamide copolymer;
       1-5% by weight of cocamidopropyl PG-dimonium chloride;
       0.01-0.05% by weight of Polyquaternium 11; and
       0.001-0.01% by weight of guar hydroxypropyltrimonium chloride; and
    95.0-97.5% by weight of a cosmetically acceptable carrier to create a spray-on solution that can be applied over top of said fragrance-bearing product.

12. The fragrance extending product of claim 11 wherein said fragrance treatment complex comprises:
    97.22% by weight of acrylates/octylacrylamide copolymer;
    0.03% by weight of Polyquaternium 11;
    0.006% by weight of guar hydroxypropyltrimonium chloride; and
    2.74% by weight of cocamidopropyl PG-dimonium chloride.

13. The fragrance extending product of claim 11 wherein said cosmetically acceptable carrier comprises:
    denatured alcohol;
    Bergamotta Oil;
    Vitamin E;
    Isododecane; and
    a lipophilic complex.

14. The fragrance extending product of claim 13 wherein said lipophilic complex comprises one or more of:
    *Glycine Soja* (Soy) Oil;
    *Vitis Vinifera* (Grapeseed) Oil;
    *Prunus Armeniaca* (Apricot) Kernel Oil;
    *Carthamus Tinctorius* (Safflower) Seed Oil;

*Borago Officinalis* (Borage) Seed Oil;
*Oenothera Biennis* (Evening Primrose) Oil; and
*Linum Usitatissimum* (Flax Linseed) Oil.

15. The fragrance extending product of claim 14 comprises:
   95.35% by weight of denatured alcohol;
   3.50% by weight of acrylates/octylacrylamide copolymer;
   0.75% by weight of Bergamotta Oil;
   0.1% by weight of Isododecane;
   0.1% by weight of said lipophilic complex;
   0.1% by weight of Vitamin E; and
   0.1% by weight of a polymer solution.

16. The fragrance extending product of claim 15 wherein said polymer solution comprises three of the four components of the components of the fragrance treatment complex, including said Polyquaternium 11, said guar hydroxypropyltrimonium chloride, and said cocamidopropyl PG-dimonium chloride.

17. The fragrance extending product of claim 16 wherein said fragrance extending product is created by placing the denatured alcohol into an appropriately sized vessel with a lightening mixer set on slow speed until a vortex is generated; then adding the acrylates/octylacrylamide copolymer slowly to the denatured alcohol with a sifter and allowed to melt thoroughly; then adding the Bergamotta Oil followed by the addition of Isododecane, the lipophilic complex, Vitamin E, and the polymer solution.

18. The fragrance extending product of claim 17 wherein said polymer solution is created by placing the cocamidopropyl PG-dimonium chloride into an appropriately sized vessel with a lightening mixer set on slow speed until a vortex is generated, then adding the Polyquaternium 11 slowly and allowed to thoroughly melt before adding the guar hydroxypropyltrimonium chloride slowly with a sifter and mixing thoroughly.

19. A fragrance-bearing product, comprising:
   2.5-5.0% by weight of a fragrance treatment complex including:
      95-99% by weight of acrylates/octylacrylamide copolymer;
      1-5% by weight of cocamidopropyl PG-dimonium chloride;
      0.01-0.05% by weight of Polyquaternium 11; and
      0.001-0.01% by weight of guar hydroxypropyltrimonium chloride;
   a perfume oil in the amount of 1.0-15.0% by weight;
   an additional quantity of Polyquaternium 11 in the amount of 0.5-1.5% by weight; and
   78.5-96.0% by weight of a cosmetically acceptable carrier.

* * * * *